United States Patent
Campos-González et al.

(10) Patent No.: US 6,680,208 B1
(45) Date of Patent: Jan. 20, 2004

(54) RAPID PROTEIN IDENTIFICATION USING ANTIBODY MIXTURES

(75) Inventors: Roberto Campos-González, Lexington, KY (US); Steven Darrell Hume, Lancaster, KY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/444,210

(22) Filed: Nov. 19, 1999

(51) Int. Cl.$^7$ ............................................. G01N 33/553
(52) U.S. Cl. ..................... 436/518; 436/528; 436/529; 436/530; 436/532; 436/535; 436/541; 436/824; 435/7.1; 435/4; 435/7.92; 435/287.3; 435/288.6; 422/56; 422/63; 422/68.1; 422/70; 204/450; 204/451; 204/452; 204/455; 204/456; 204/546; 356/344
(58) Field of Search ................................. 436/518, 528, 436/529, 530, 532, 535, 541, 824; 435/4, 7.1, 7.92, 287.3, 288.6; 422/56, 63, 68.1, 70; 204/450, 451, 452, 455, 456, 546; 356/344; D24/233

(56) References Cited

U.S. PATENT DOCUMENTS

| 3,901,782 A | * | 8/1975 | Vadasz et al. | 204/180 |
| 4,130,471 A | * | 12/1978 | Grunbaum | 204/180 |
| 4,385,974 A | * | 5/1983 | Shevitz | 204/180 |

(List continued on next page.)

OTHER PUBLICATIONS

Anderson and Davison, "Multiplex Western Blotting System for the Analysis of Muscular Dystrophy Proteins." Am. J. Path. 154:1017–22, 1999.

Faleiro et al., "Multiple species of CPP32 and Mch2 are the major active caspases present in apoptotic cells." EMBO J. 16:2271–81, 1997.

Kapfhammer, "Protein blotting analysis of large sample numbers." Electrophoresis. 14:881–5, 1993.

Krajewski et al., "Detection of Multiple Antigens on Western Blots." Anal. Biochem. 236:221–8, 1996.

(List continued on next page.)

Primary Examiner—Christopher L. Chin
Assistant Examiner—Pensee T. Do
(74) Attorney, Agent, or Firm—Douglas A. Petry

(57) ABSTRACT

A method and device is disclosed for rapidly identifying a large number of proteins by placing a protein mixture in a sample chamber of an electrophoresis gel, and performing electrophoresis to separate the mixture by molecular weight, in a direction of separation, into a two-dimensional separation pattern in the gel. The separation pattern is transferred to a membrane, such as a sheet of nitrocellulose, and a plate with a set of separate, side-by-side slots is then applied to the membrane. A different antibody mixture is introduced into each of the slots by perfusing each antibody mixture under pressure through the slots. The antibody mixture that is perfused through each slot recognizes several different proteins of sufficiently different molecular weights that different protein bands can be resolved by the antibody mixture in each slot. Proteins of similar molecular weights are recognized by antibody mixtures perfused through different slots, such that otherwise overlapping protein bands are detected in different lanes. The positions of protein bands in each of the lanes are correlated with expected positions of proteins recognized by the mixture for that lane, and the presence of a band is correlated with the presence of the corresponding protein in the mixture. It is emphasized that this abstract is provided to comply with the rules requiring an abstract which will allow a searcher or other reader to quickly ascertain the subject matter of the technical disclosure. It is submitted with the understanding that it will not be used to interpret of limit the scope or meaning of the claims.

37 Claims, 9 Drawing Sheets

U.S. PATENT DOCUMENTS

| | | | | |
|---|---|---|---|---|
| 4,443,319 A | * | 4/1984 | Chait et al. | 204/299 |
| 4,452,901 A | * | 6/1984 | Gordon et al. | 436/506 |
| 4,483,885 A | * | 11/1984 | Chait et al. | 427/58 |
| 4,512,896 A | * | 4/1985 | Gershoni | 210/635 |
| 4,668,363 A | | 5/1987 | Gebott et al. | |
| 4,681,853 A | | 7/1987 | Hardy et al. | |
| 4,713,349 A | | 12/1987 | Levin | |
| 4,834,946 A | | 5/1989 | Levin | |
| 4,863,647 A | * | 9/1989 | Baylor, Jr. | 264/22 |
| 4,867,855 A | * | 9/1989 | Burton | 204/182.8 |
| 4,874,490 A | * | 10/1989 | Hochstrasser | 204/182.1 |
| 4,874,492 A | * | 10/1989 | Mackay | 204/182.8 |
| 4,909,918 A | * | 3/1990 | Bambeck et al. | 204/299 |
| 4,939,098 A | | 7/1990 | Suzuki et al. | |
| 4,975,174 A | * | 12/1990 | Bambeck et al. | 204/299 |
| 4,978,507 A | | 12/1990 | Levin | |
| 5,019,232 A | * | 5/1991 | Wilson et al. | 204/182.8 |
| 5,133,866 A | * | 7/1992 | Kauvar | 210/635 |
| 5,167,790 A | * | 12/1992 | Carle et al. | 204/299 |
| 5,228,960 A | | 7/1993 | Liu et al. | |
| 5,240,577 A | * | 8/1993 | Jorgenson et al. | 204/180.1 |
| 5,264,101 A | * | 11/1993 | Demorest et al. | 204/299 |
| 5,320,727 A | | 6/1994 | Jackson | |
| 5,356,772 A | | 10/1994 | Chan et al. | |
| 5,407,546 A | * | 4/1995 | Schickle | 204/182.1 |
| 5,536,382 A | | 7/1996 | Sunzeri | |
| 5,569,369 A | | 10/1996 | Leffler et al. | 204/620 |
| 5,611,903 A | | 3/1997 | Janssens et al. | 204/454 |
| 5,637,202 A | | 6/1997 | Harrington et al. | 204/469 |
| 5,650,299 A | * | 7/1997 | Lawman et al. | |
| 5,653,859 A | | 8/1997 | Parton et al. | |
| 5,773,645 A | | 6/1998 | Hochstrasser | 204/456 |
| 5,837,116 A | | 11/1998 | Harrington et al. | 204/606 |
| 5,882,495 A | * | 3/1999 | Garrels | 204/456 |
| 5,916,427 A | * | 6/1999 | Kirkpatrick | 204/469 |
| 5,989,400 A | * | 11/1999 | Islam | 204/466 |
| 5,993,627 A | * | 11/1999 | Anderson et al. | 204/456 |
| 6,048,715 A | * | 4/2000 | Haynes et al. | 435/179 |
| 6,123,821 A | * | 9/2000 | Anderson et al. | 204/456 |
| 6,136,173 A | * | 10/2000 | Anderson et al. | 204/461 |

OTHER PUBLICATIONS

Lee et al., "A rapid multicolor Western blot." J. Immunol. Meth. 106:27–30, 1988.

Lin and Pagano, "Sequential Detection of Different Antigens Induced by Epstein–Barr Virus and Herpes Simplex Virus in the Same Western Blot by Using Dual Antibody Probes." J. Virol. 59:522–4, 1986.

Mischak et al., "Monoclonal antibodies against different domains of cellobiohydrolase I and II from *Trichoderma reesei*." Biochim. Biophys. Acta. 990:1–7, 1988.

Sanchez et al., "Simultaneous analysis of cyclin and oncogene expression using multiple monoclonal antibody immunoblots." Electrophoresis. 18:638–41, 1997.

Theisen et al., "Sequential detection of antigens in Western blots with differently colored products." Anal. Biochem. 152:211–4, 1986.

* cited by examiner

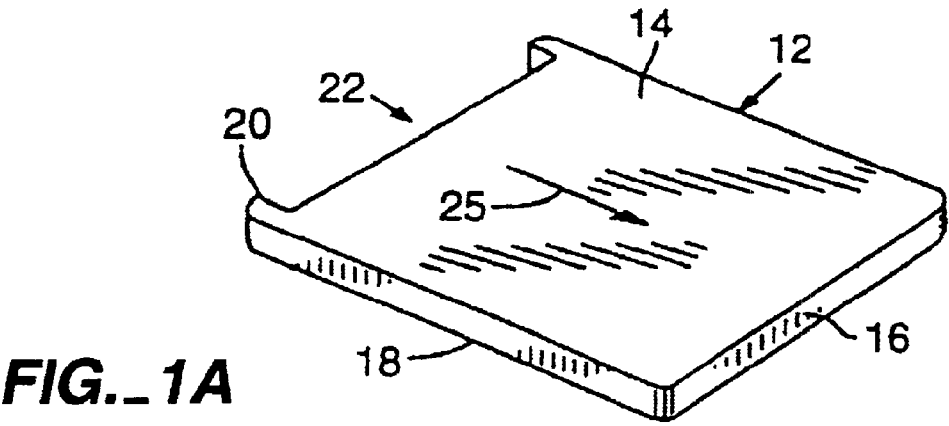
FIG._1A
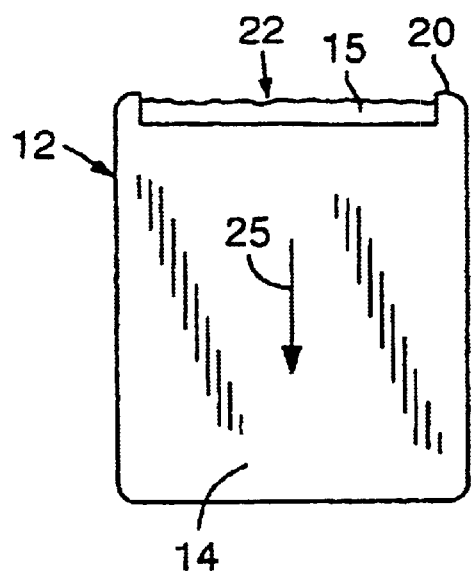
FIG._1B
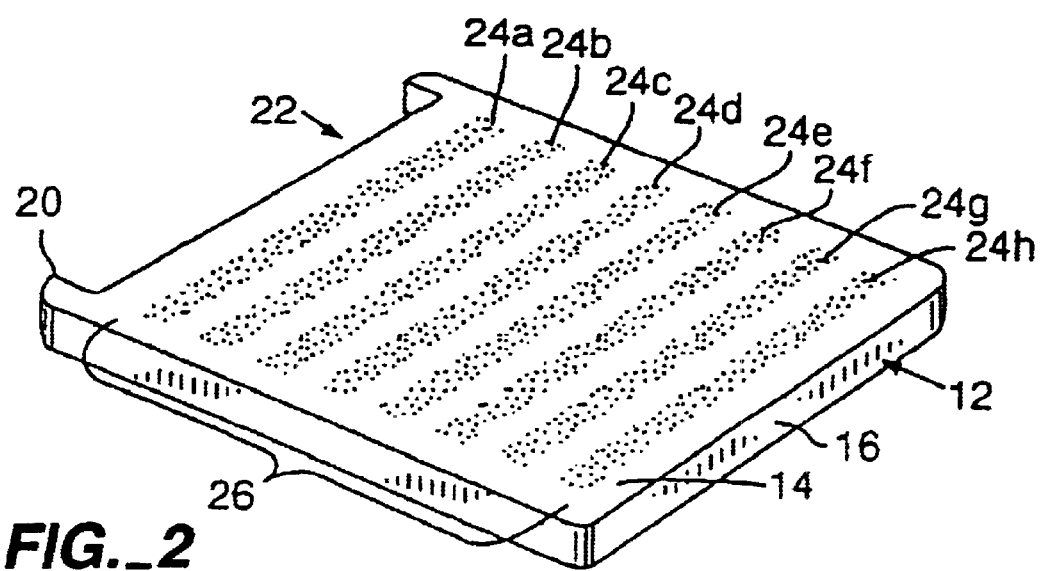
FIG._2

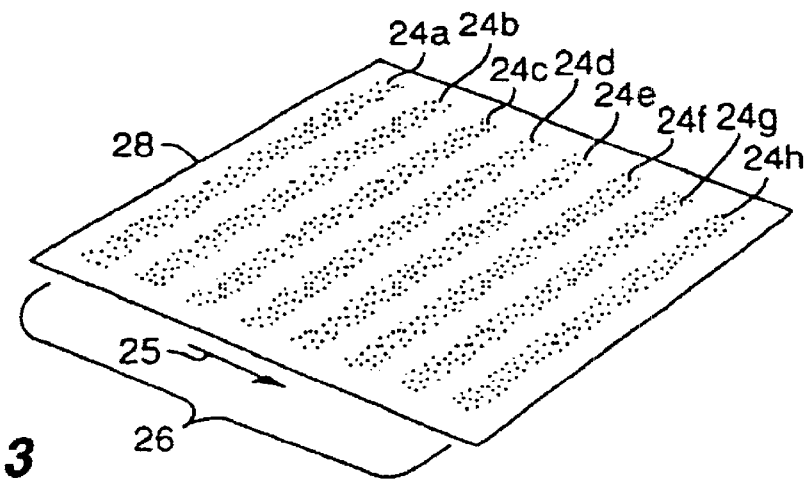
FIG._3
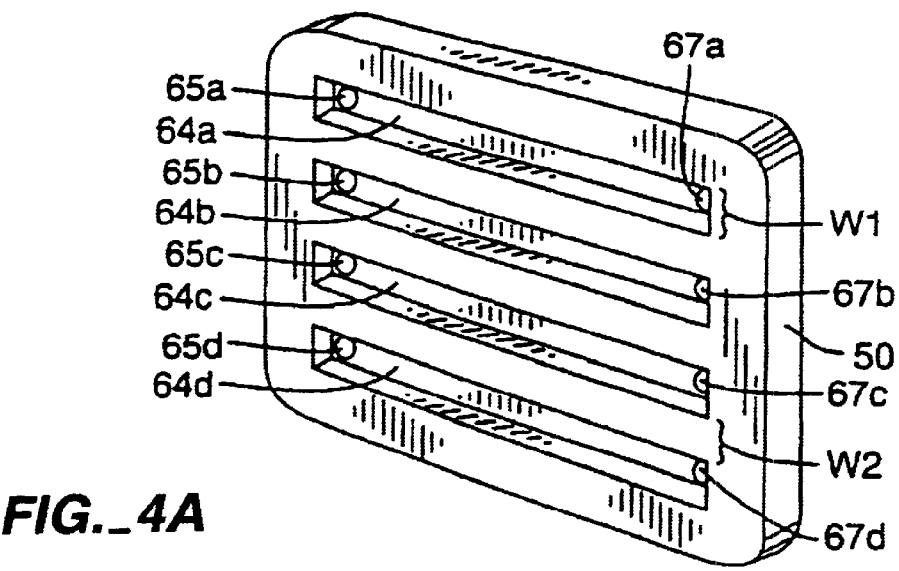
FIG._4A
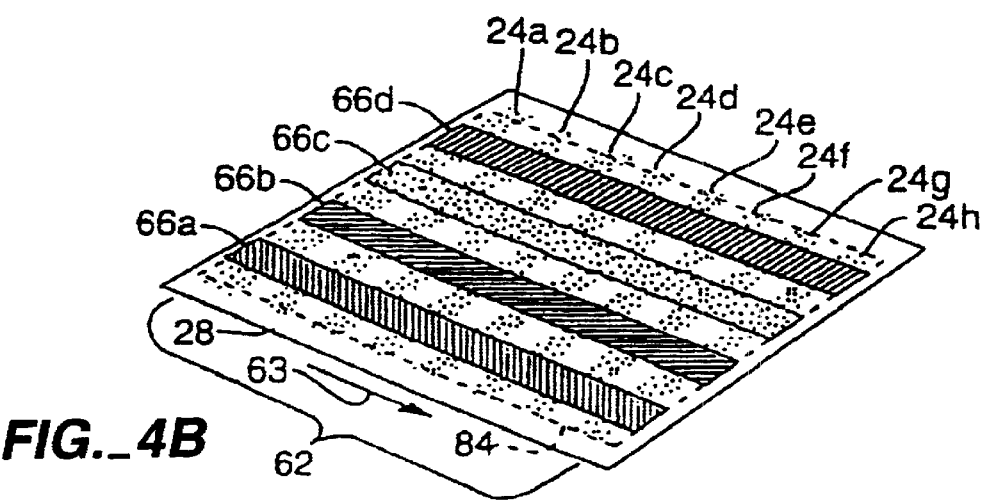
FIG._4B

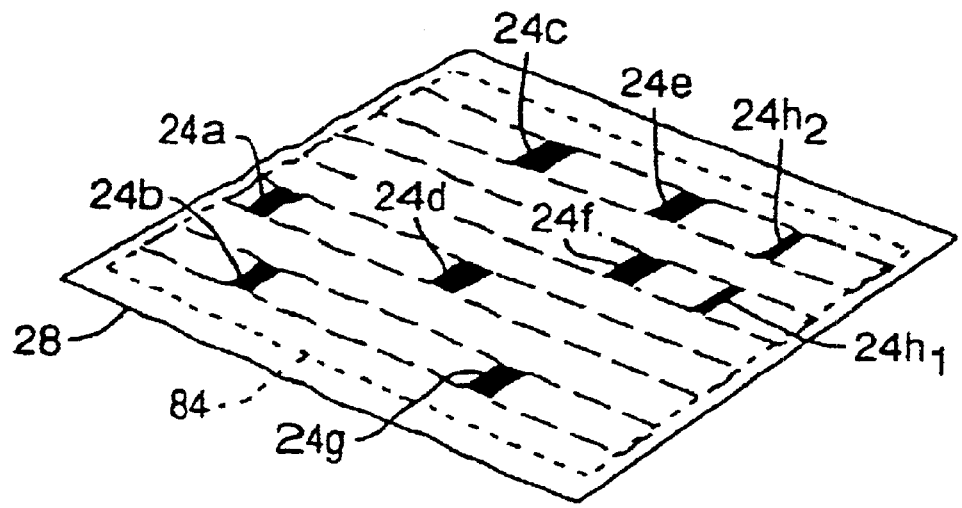
FIG._5
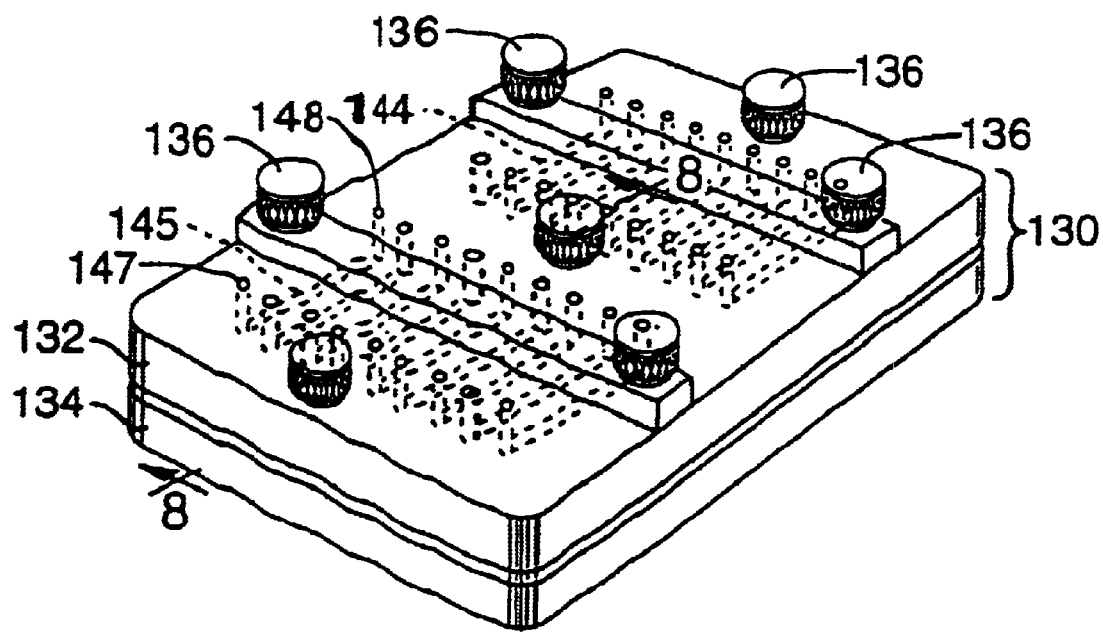
FIG._6

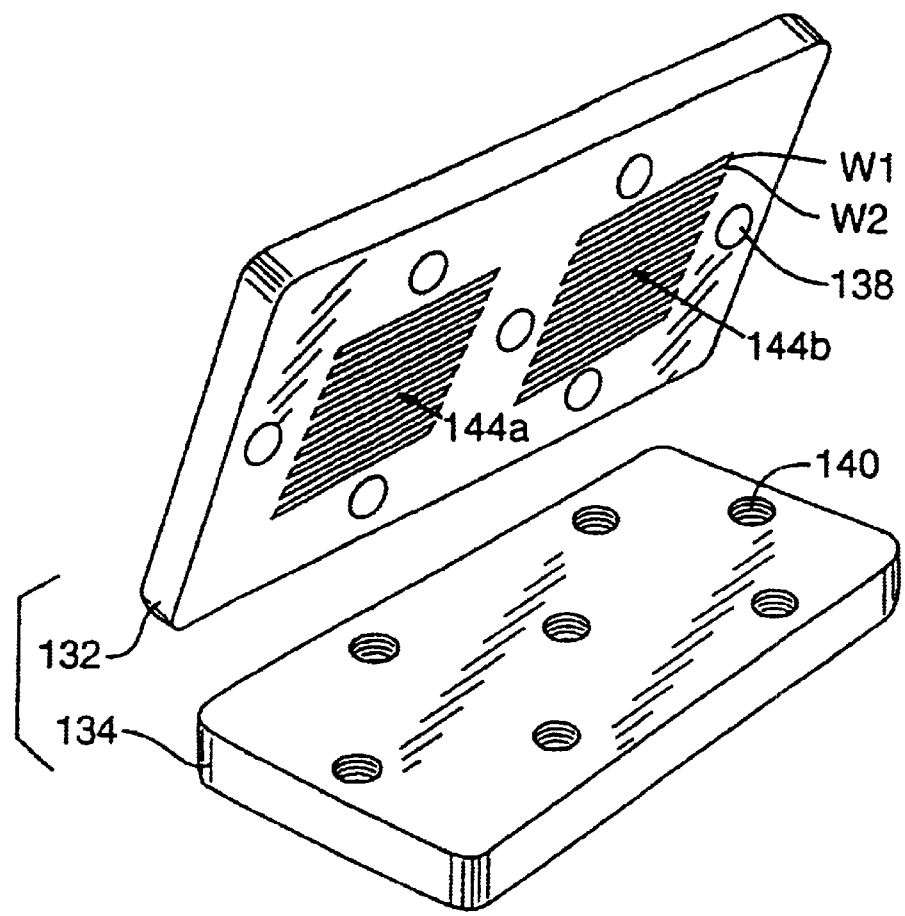
FIG._7
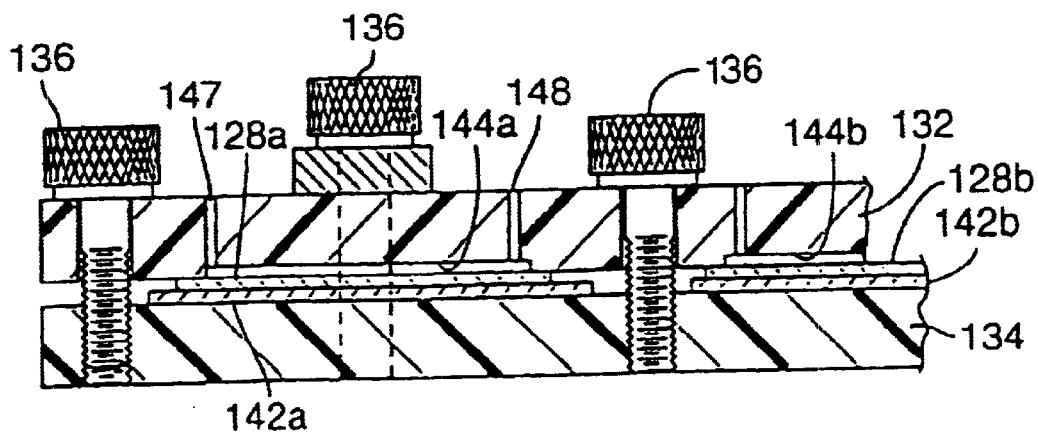
FIG._8

FIG._9A

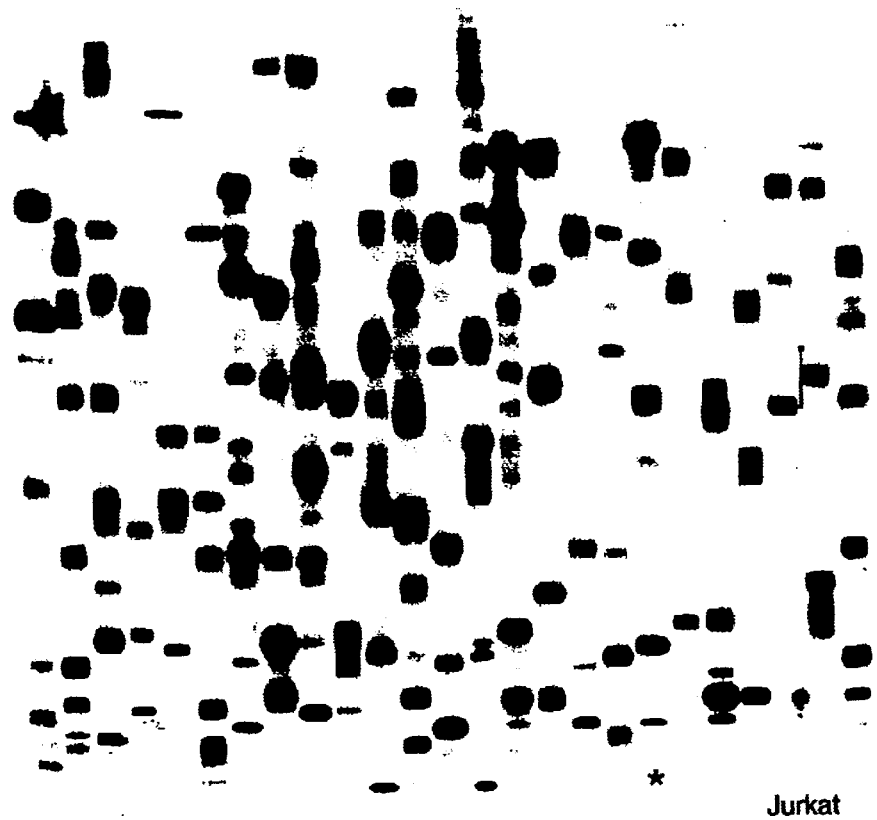
FIG._9B

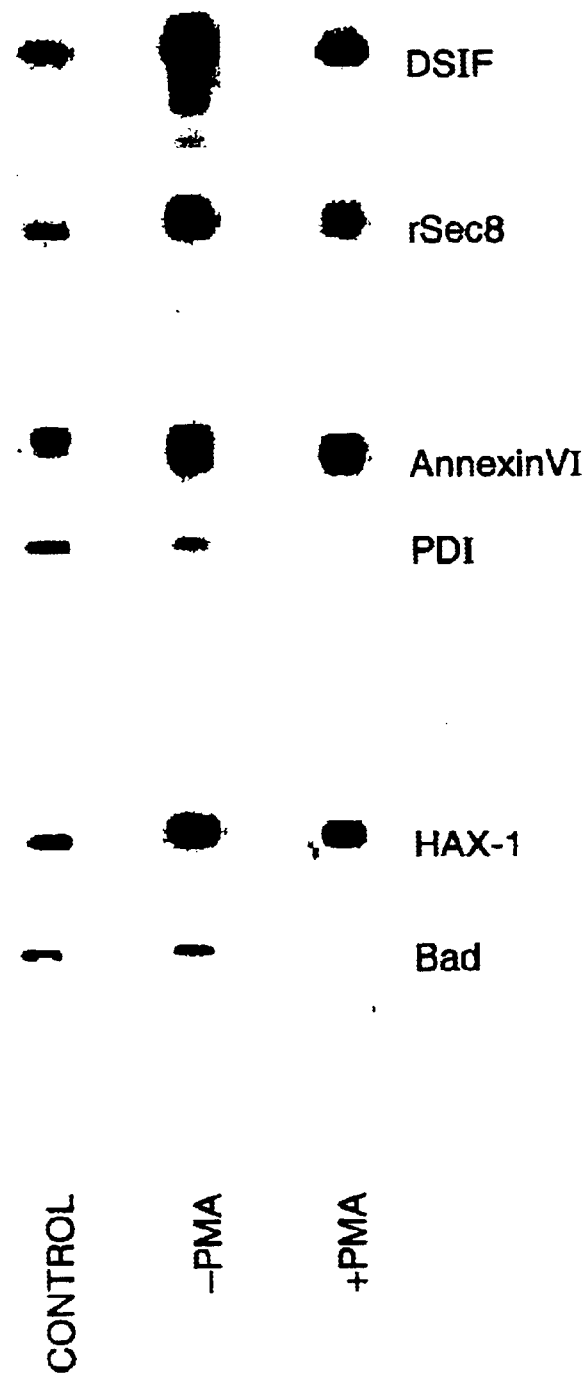
FIG._10A

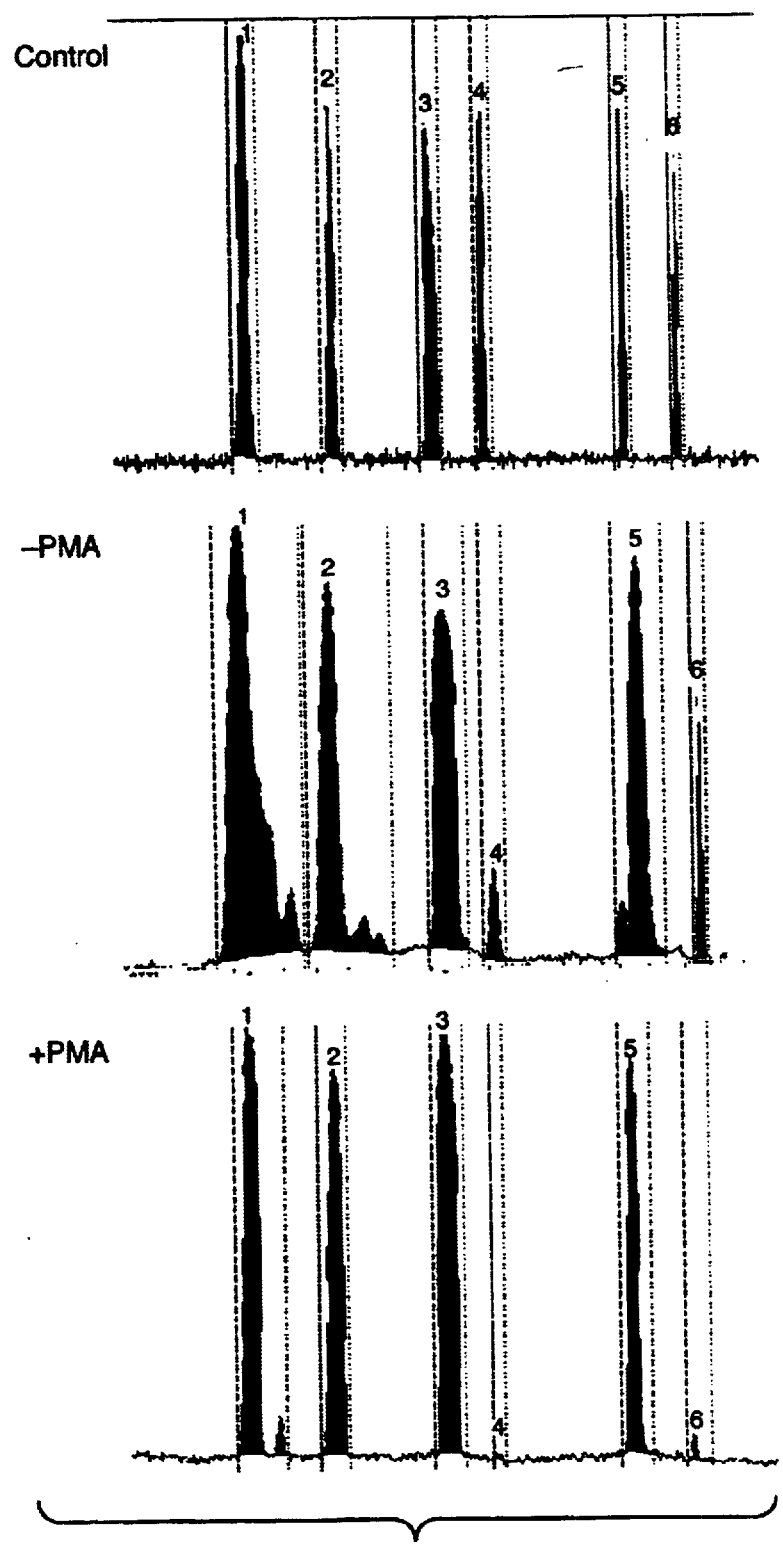
FIG._10B

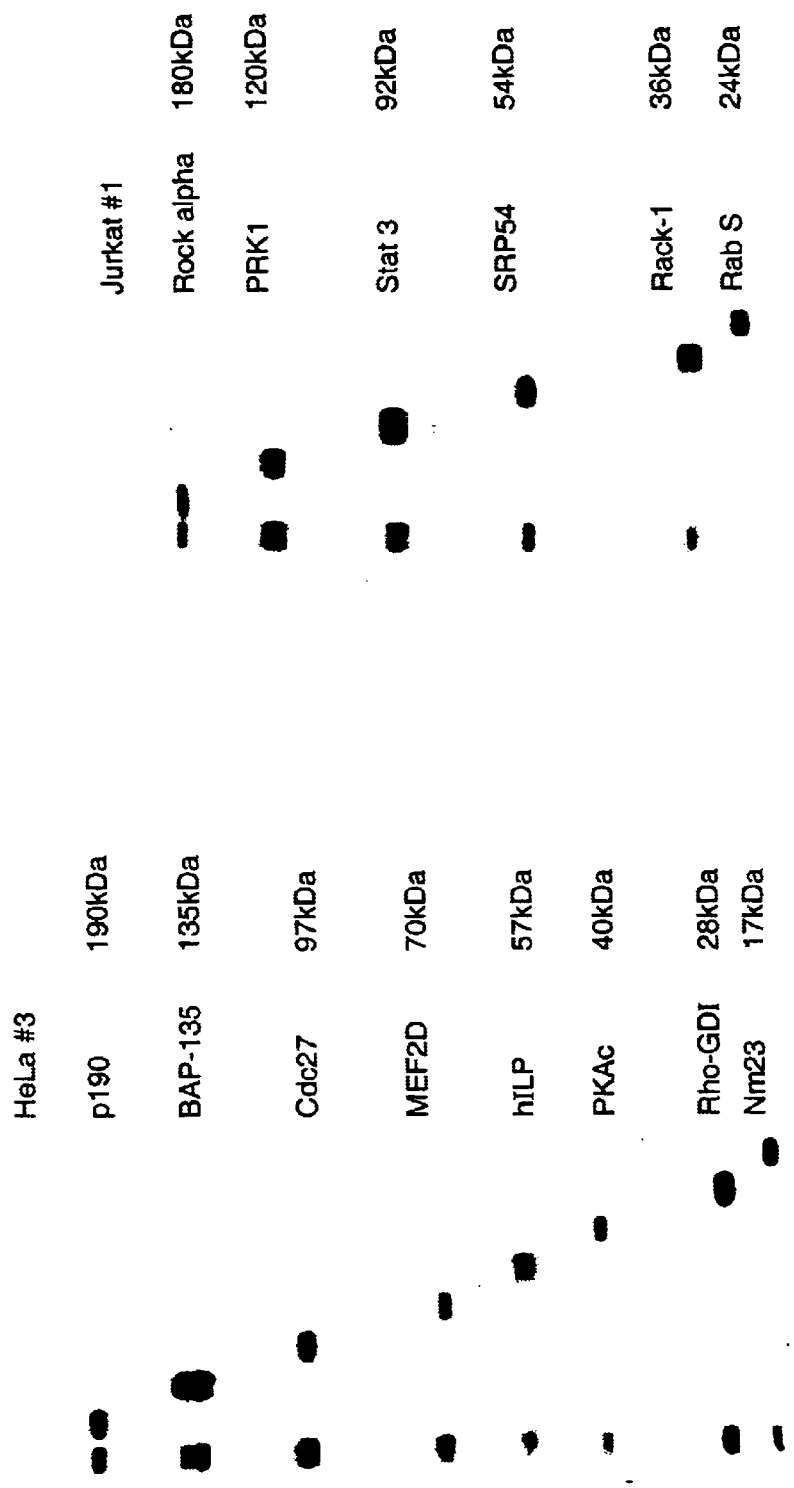

RAPID PROTEIN IDENTIFICATION USING ANTIBODY MIXTURES

FIELD

This invention relates to a method for identifying proteins in a protein mixture using electrophoresis.

BACKGROUND

Immunoassay systems have long been used to analyze proteins. Such methods include traditional Western blotting, in which a sample is subjected to SDS-polyacrylamide gel electrophoresis (SDS-PAGE), which resolves the individual proteins present in the sample by their molecular weights. The proteins (antigens) in the gel are subsequently transferred to a membrane, which is exposed to an antibody-containing solution. The antibody recognizes a specific protein, which allows the protein of interest to be identified. To detect this interaction, a secondary antibody containing a detectable marker is added. Typically, this procedure is used to detect only one protein on a membrane.

With conventional techniques, protein blotting is not well suited to handle large numbers of proteins. Traditionally, to analyze several different proteins simultaneously, individual lanes of the sample are run on a gel and the proteins are transferred to a membrane which is cut into a series of strips (each strip containing the samples). Each of the individual membrane strips are incubated with a different antibody-containing solution. This requires that each strip be handled separately, which is a very laborious and tedious task.

The detection of multiple proteins on a single gel using sequential probes has been described. In these methods, samples are resolved using SDS-PAGE, transferred to membranes, and exposed to primary and color-conjugated secondary antibodies. The resulting bands of differently colored products allow for the identification of several antigens on a single lane of a blot. In one variation of the method (Krajewski et al., 1996, *Anal. Biochem.* 236:221–8; Lin and Pagano, 1986, *J. Virol.* 59:522–4; and Theisen et al., 1986, *Anal. Biochem.* 152:211–4), the membrane is exposed to one primary antibody, which is detected with a colored-secondary antibody, producing a colored reaction. The blot is subsequently reprobed with different primary and colored-secondary antibodies, producing a colored reaction different from the first.

In another variation of this method, Lee et al. (*J. Immunol. Meth.* 106:27–30, 1988) describes the simultaneous probing of different proteins. This method requires the use of primary antibodies generated in different species, for example one antibody made in rabbits (i.e. polyclonal), the other in mice (i.e. monoclonal), which are added to the membrane at the same time. The differently color-conjugated secondary antibodies (anti-rabbit or anti-mouse), will bind to only one of the primary antibodies. This allows for the detection of at least two different proteins simultaneously.

The use of two-dimensional (2D) gel electrophoresis to detect multiple proteins on a single blot has been reported. Sanchez et al. (*Electrophoresis.* 18:638–41, 1997) discloses the use of a monoclonal antibody mixture to detect nine individual proteins which are sufficiently different in both pI and molecular weight to avoid ambiguities in their identification. Faleiro et al. (*EMBO J*. 16:2271–81, 1997) teaches the use of 2D gel electrophoresis to detect multiple caspases. Three U.S. Patents to Levin (U.S. Pat. Nos. 4,713,349, 4,834,946, and 4,978,507) describe an apparatus that can be used to detect multiple antigens on a single protein-containing membrane. The apparatus includes an upper and lower plate, between which a protein-containing membrane is placed. The upper plate contains an array of channels, into which an antibody-containing liquid is introduced.

SUMMARY

The present invention provides an improved method for detecting and quantitating proteins present in a sample. The present invention allows several proteins to be identified and/or quantitated in the same sample, overcoming many of the limitations of current immunoassay systems. In certain particular examples, multiple proteins in the sample can be identified simultaneously.

The present invention provides a method for identifying different proteins in a protein mixture sample by electrophoretically separating proteins by molecular weight from at least one sample into at least a two-dimensional molecular weight gradient pattern in a direction of separation on a gel. The molecular weight gradient pattern is exposed simultaneously or sequentially to a plurality of adjacent, elongated specific binding agent applicators that extend in the direction of separation. Each applicator applies a plurality of different sets of specific binding agents in different lanes, wherein each set recognizes proteins of sufficiently different molecular weights to distinguish different proteins from one another along the direction of separation. Proteins in the mixture that have similar molecular weights are recognized in different lanes, such that otherwise partially or completely overlapping protein bands are detected in different lanes.

The proteins may be electrophoretically separated by introducing the protein mixture into an elongated sample chamber that extends transverse to the direction of separation, and performing electrophoresis to separate the proteins in the direction of separation by molecular weight. There can be at least three (for example at least ten) applicators, each of which applies at least 2, 5, 10, or 50 different specific binding agents. In one embodiment, the applicators are substantially parallel. The applicators may be slots or elongated channels having slots through which the specific binding agents are applied. Alternatively, each applicator may include multiple, closely spaced nozzles or holes in place of the elongated slot. In a further embodiment, the ratio of different specific binding agents applied to the number of elongated applicators is at least 1 or 3 different specific binding agents to each applicator (for example at least 5 or more different specific binding agents).

In a particular embodiment, the specific binding agent is an antibody, such as a monoclonal antibody. The specific binding agents may recognize signal transduction proteins. In another embodiment, the protein mixture sample includes a cell lysate.

In disclosed embodiments, the pattern is transferred from the gel to a transfer member, and the different sets of specific binding agents are applied to the transfer member. The method may also include detecting a location of binding of specific binding agents, and correlating each location with a particular specific binding agent that identifies a protein of interest. In a further embodiment, the method includes quantitating the protein of interest, for example by measuring intensity or luminescence, after detecting the protein of interest.

The cell lysate sample can be introduced into an elongated sample trough in an electrophoresis gel. Electrophoresis is performed on the sample to separate the cell lysate from the elongated sample chamber into a molecular weight gradient pattern in a direction of separation that extends transverse to the sample chamber. The pattern is transferred to a transfer member, and subsequently exposed simultaneously to a plurality of adjacent, elongated antibody applicator channels having slots that extend in the direction of separation, substantially transverse to the sample chamber. The plurality of different applicators apply different sets of specific binding agents to the transfer member in side-by-side lanes. The specific binding agents within each slot recognize proteins of distinguishable molecular weights, and the specific binding agents in different slots are sufficiently different to recognize a variety of different proteins of interest. Proteins that are of similar molecular weights, and would otherwise partially or completely overlap in a single lane, are detected in separate lanes. Each location where a protein is detected may then be correlated with a particular specific binding agent that identifies a protein of interest, by comparing a detected location of binding with an expected location of binding for each applicator. In a particular embodiment, there are at least fifty different specific binding agents, applied in at least three different sets (for example at least ten sets of three binding agents) by the applicators.

The present invention also provides a method for simultaneously analyzing a plurality of different proteins in a sample by subjecting the sample to electrophoresis, thereby separating the plurality of different proteins by molecular weight into a field that has at least two dimensions (which means that a three dimensional field could also be used). The plurality of different proteins are transferred and immobilized on a transfer member. The member is exposed simultaneously or sequentially to different sets of specific binding agents. For example, a plate containing several discrete slots is placed against the transfer member wherein different slots contain different sets of antibody-containing mixtures. Each antibody-containing mixture is exposed to the surface of the transfer member for a sufficient period of time for the antibody to bind to a protein of interest if the protein is present in the transfer member. The bound antibodies are detected to locate proteins of interest in the transfer member, and positions of the proteins are correlated with expected locations of binding of known reference proteins.

In a particular embodiment, the transfer member is a protein transfer membrane, such as nitrocellulose, and the sample is a cell lysate. In a further embodiment, the antibodies recognize signal transduction proteins. In yet a further embodiment, each antibody-containing mixture contains at least two (for example at least three, six or ten) different antibodies. In specific examples, the total number of different antibodies applied to each membrane can range from 50–250, or more. In another embodiment, the ratio of different sets of antibody mixtures (in which at least one of the antibodies in the mixture recognize a different protein) to the number of channels is 1:1, and the number of antibodies in each channel ranges from 2 to 10 or 1 to 20. In a further embodiment, the plate (or a series of plates) contains at least four, ten, eighteen, twenty or fifty different channels. In another embodiment, the proteins of interest range in molecular weight from 10 kDa–300 kDa.

The present invention also provides a system for identifying different proteins in a protein mixture sample which includes an applicator plate which has several applicators, a liquid supply line that communicates with each applicator and a set of different antibody mixtures. The different antibody mixtures communicate with different supply lines. Each of the different antibody mixtures contains antibodies that recognize proteins that do not substantially overlap on an electrophoresis gel, and that recognize proteins that would overlap on the electrophoresis gel.

In a particular embodiment, the system has one or more pumps for introducing the different antibody mixtures into the supply lines and through the applicators. In a specific embodiment, the system also has a scanner that detects bands on a substrate that has been exposed to the antibody mixtures. An image of the bands on the substrate may be recorded by the scanner. In other embodiments, the system is automated to introduce the antibody mixtures through the applicators.

In a further embodiment, the systems contains a reference image source that includes expected locations of bands that would be detected for each antibody mixture if a protein or proteins detected by the antibody mixture is present in the protein mixture. The reference image source can be stored in a computer readable medium. The present invention further includes the computer readable medium in which the reference image is stored.

The present invention also provides a device for identifying proteins that have been separated into a field of separation by electrophoresis. The device has an exposure means for exposing the substrate to several different elongated applicators and a supply means for supplying different sets of antibody mixtures to different applicators. A set of antibody mixtures supplied to a first applicator recognizes proteins of sufficiently different molecular weight to be separately resolved along a path of exposure of the first applicator. In a particular embodiment, the exposure means simultaneously exposes the substrate to several different elongated applicators. In another embodiment, the set of antibody mixtures which is supplied to one applicator recognizes a protein that is not of a substantially different molecular weight to be separately resolved from a protein recognized by the antibody mixture supplied to another applicator.

The foregoing, and other features and advantages of the invention, will become apparent from the following detailed description of several embodiments, which proceeds with reference to the accompanying figures.

BRIEF DESCRIPTION OF THE FIGURES

FIG. 1 is a separation gel containing an elongated sample chamber. Two views are shown: (A) a top perspective view with the gel in the horizontal position and (B) a front perspective view with the gel in a vertical position. This gel serves to separate the proteins by their molecular weights when an electric current is applied.

FIG. 2 is a view similar to FIG. 1A, showing a schematic drawing of a molecular weight gradient pattern generated in the gel from a sample containing nine proteins.

FIG. 3 is a schematic representation of a molecular weight gradient pattern after it has been electrophoretically transferred to a transfer member.

FIG. 4A perspective view of a the device having four elongated applicators in a cover plate, and FIG. 4B shows a schematic representation of different sets of antibody mixtures applied to the transfer member using the device shown in FIG. 4A.

FIG. 5 shows a schematic representation of a transfer member that has been simultaneously probed with the antibody mixtures to simultaneously identify nine proteins.

FIG. 6 is a top perspective view of an assembled apparatus for rapidly identifying separated proteins.

FIG. 7 is a perspective view of the device shown in FIG. 6, with the cover plate and base plate separated from each other, and showing the elongated applicators in the cover plate.

FIG. 8 is an enlarged, fragmentary, cross-sectional, elevational view taken in the direction of arrows 8—8 of FIG. 6.

FIG. 9 is a digital image of two transfer members that have been subjected to the protein identification method of the present invention, showing the result of an experiment in which numerous proteins were identified simultaneously in Jurkat cells incubated with (A) or without (B) PMA.

FIG. 10 is a digital image of the (A) transfer members and a (B) graphical representation thereof, of the control transfer member and the portion of the transfer member containing the lanes of FIG. 9 (* lanes in FIG. 9A and 9B) to which the control was compared.

FIG. 11 is a digital image of transfer members showing two antibody mixtures that were tested in (A) HeLa cells and (B) Jurkat cell lystates.

DETAILED DESCRIPTION OF SEVERAL EMBODIMENTS

Abbreviations and Definitions

The following definitions and methods are provided to better define the present invention and to guide those of ordinary skill in the art in the practice of the present invention. It must be noted that as used herein and in the appended claims, the singular forms "a" or "an" or "the" include plural referents unless the context clearly dictates otherwise. Thus, for example, reference to "a protein" includes a plurality of such proteins and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs.

Applicator: Applicators can include discrete slots or elongated channels, a series of closely spaced holes aligned in a row, or any other configuration that permits a substantially continuous application of specific binding agents, such as an antibody mixture, to a substrate. A substantially continuous applicator is one that allows the proteins of interest to be identified. The specific binding agents are applied through the applicators.

Cell lysate: A mixture resulting from the decomposition, breakdown or lysis of cells or tissue. Also includes any mixture of proteins of natural or synthetic origin.

Database of predicted locations: A database showing the predicted position on a gel or transfer member, of the proteins which are recognized by a particular set of specific binding agents. This database is used to determine which proteins recognized by a particular set of specific binding agents are expressed in the experimental sample.

Detection: The method of detecting the electrophoretically separated proteins. Such methods may include, but are not limited to, colorimetric, densitometry, enhanced chemiluminescence (ECL) and radiography. The signal generated by the protein(s) of interest may be recorded, for example, on film or a phosphoimager screen.

Detected location: The position of the protein on the gel or transfer member.

MINIBLOTTER Device: An apparatus described in U.S. Pat. No. 4,834,946, which patent is incorporated by reference.

Different sets of specific binding agents: Multiple mixtures each containing multiple specific binding agents, for example 2–10 individual specific binding agents, wherein at least some (and in some embodiments all) of the sets are unique sets. Unique sets include sets that have at least one antibody different from (or in addition to) antibodies in any other set. In particular embodiments, the unique sets are substantially different, with no set having more than one antibody that appears in other sets. In some very particular embodiments, each of the sets are unique, not having any antibodies that are the same as (or recognize the same protein as) an antibody in any other set. Each mixture can recognize a unique population of proteins, for example as shown in FIGS. 11A and 11B and in Table 2 .

ECL: Enhanced chemiluminescence.

Electrophoresis gel: A colloidal system, with the semblance of a solid, in which a solid is dispersed in a liquid. The solid can include, but is not limited to, such materials as BIS/acrylamide or agarose. The amount or percentage of acrylamide can be varied within the gel (gradient gel) or between gels (for example using lower percentage gels to resolve larger higher-molecular weight proteins, and higher percentage gels to resolve smaller lower-molecular weight proteins). One skilled in the art will know how to choose a gel system that works best for resolving the proteins of interest.

Electrophoretic separation: The separation technique which separates charged units, such as proteins, on the basis of differential mobility in an electric field. The electrical field depends on the size, shape, and charge of the units. The method is widely used for separation of proteins and other materials.

Electrophoretic transfer: A method used to transfer proteins from the separation gel to a transfer member, such as nitrocellulose, diethylaminoethyl-(DEAE-) cellulose membrane, or PVDF membrane, or to diazobenzyloxymethyl-(DBM-) or diazophenylthioether-(DPT-) paper by electrophoresis, resulting in the membrane or paper bearing a resultant pattern of separated proteins.

Elongated sample chamber: Also known as the "well" or "wells" of a gel, this is the region of the gel into which the protein mixture sample is loaded.

Molecular weight gradient pattern: The pattern of bands produced in the gel after subjecting proteins to an electric field. Proteins are resolved by their molecular weight, with smaller lower molecular weight proteins moving faster through the gel than larger higher molecular weight proteins.

Potential or predicted location: The previously determined position of proteins on a gel or transfer member, corresponding to proteins identified by each set of specific binding agents. This predicted location of the proteins is compared to the unknown, experimental sample, to identify proteins separated by electrophoresis from a protein mixture.

Protein mixture sample: A sample containing at least two proteins.

Quantitation: A method of determining the relative amount of one or more proteins in a sample. Quantitation can be performed using densitometry, wherein the amount of signal generated from a protein in one sample is compared to the amount of signal generated from the same protein in another sample. Commercial suppliers of devices, and such software for performing densitometry, include Bio-Rad GS-525 Molecular Imager System with Molecular Analyst v.2.1 (Bio-Rad Laboratories, Hercules, Calif.) and UMAX Astra 1200S digital Scanner with UN-Scan-IT gel v.3.1 (Silk Scientific, Orem, Utah).

Sample: A specimen to be analyzed by the present method, such specimens include cell lysates generated from tissue culture cells, such as those that can be obtained from The American Type Culture Collection, A.T.C.C. (Manassis, Va.). Potential samples also include physiological samples, such as whole blood, plasma, serum, urine, cerebrospinal fluid, pathology specimens, needle aspirates and biopsies. Also includes any other mixture of proteins either of natural or synthetic origin.

Signal transduction protein: A protein involved in the transfer of a signal from the outside to the inside of a cell by means other than the introduction of the signal molecule itself into the cell. Typically, interaction of the extracellular signal, such as hormones or growth factors, leads to the synthesis within the cell of one or more second messengers, or to activation of other downstream cascades (for example phosphorylation). Examples of signal transduction proteins include, but are not limited to those shown in FIGS. 11A and 11B and Table 2.

Specific binding agent: An agent that binds substantially only to a defined target. For example, a syntaxin 4 protein specific binding agent binds substantially only the syntaxin 4 protein, and not other proteins. As used herein, the term "specific binding agent" includes any chemical or protein that binds substantially only to a specific protein, such as antibodies or ligand-binding probes.

The term "antibodies" encompasses monoclonal and polyclonal antibodies that are specific for the protein of interest, i.e., which bind substantially only to the protein of interest when assessed using the methods described below, as well as immunologically effective portions ("fragments") thereof. Antibodies that recognize a protein of interest used in one aspect of the present invention are monoclonal antibodies (or immunologically effective portions thereof) and may also be humanized monoclonal antibodies (or immunologically effective portions thereof). Immunologically effective portions of monoclonal antibodies include Fab, Fab', F(ab")$_2$, Fabc and Fv portions (for a review, see Better and Horowitz, *Methods. Enzymol.* 1989, 178:476–96).

The determination that a particular agent binds substantially only to the protein of interest may readily be made by using or adapting routine procedures. One suitable in vitro assay makes use of the Western blotting procedure (described in many standard texts, including *Antibodies, A Laboratory Manual* by Harlow and Lane, 1988). Western blotting may be used to determine that a given binding agent, such as a monoclonal antibody, binds substantially only to the protein of interest.

Transfer member: The substrate onto which the electrophoretically separated proteins are transferred from the separating gel. Such substrates include transfer membranes, such as protein transfer membranes. Examples of such membranes include: nitrocellulose, PVDF, or diethylaminoethyl- (DEAE-) cellulose, or papers such as diazobenzyloxymethyl-(DBM-) or diazophenylthioether- (DPT-) paper.

Tumor: A neoplasm.

Neoplasm: Abnormal growth of cells.

Cancer: malignant neoplasm that has undergone characteristic anaplasia with loss of differentiation, increased rate of growth, invasion of surrounding tissue, and is capable of metastasis.

Malignant: Cells which have the properties of anaplasia invasion and metastasis.

Normal cells: Non-tumor, non-malignant cells.

DETAILED DESCRIPTION

The present invention is an improved method for detecting and quantitating several proteins in a sample, including in specific examples simultaneous detection. This method is a form of Western blotting, wherein multiple different sets of specific binding agents, such as monoclonal antibodies, are exposed to a single sample, after the sample has been resolved using electrophoresis. Each set recognizes proteins of sufficiently different molecular weights, allowing different proteins to be distinguished from one another. The location of the specific binding agents is detected and correlated with a particular specific binding agent that identifies a protein of interest. Once the proteins have been identified, the amount of the protein present at the location can also be quantitated.

FIGS. 1A and 1B show a gel 12 as a specific example of a protein separation medium, in which gel 12 has a front surface 14, a continuous peripheral face 16, and a rear surface 18. A top edge 20 of gel 12 includes an indentation or notch, formed in a known fashion, to present a sample chamber 22 into which a protein mixture 15 is placed for subsequent electrophoresis. The illustrated sample chamber 22 extends across substantially the entire top edge 20 of gel 12, but in other embodiments it could be (for example) a trough or slot placed in the front surface 14 of the gel, separate from and parallel to the top edge 20 of the gel.

In use, glass plates (not shown) are placed against the front 14 and back 18 surfaces of the gel, protein mixture 15 is placed in sample chamber 22, and an electric current is introduced through gel 12, so that proteins in the mixture 15 are electrophoretically separated by molecular weight, generating a molecular weight gradient pattern 26 (FIG. 2) that extends in a direction of separation 25 (FIG. 1). Chamber 22 extends sufficiently across gel 12 to produce a gradient pattern (FIG. 2) that is wide enough to permit multiple simultaneous analysis of the pattern with a plurality of (for example three or more) side-by-side elongated applicator slots that apply different mixtures of antibodies to the pattern 26. Hence the length of chamber 22 is at least as long as the combined width of the separate applicators.

FIG. 2 shows a hypothetical molecular weight gradient pattern 26 from a sample containing at least eight individual proteins 24a–h. For purposes of illustration, the at least eight different proteins are distinguishable from one another because they are sufficiently different in their molecular weights to be separately resolved on gel 12. In specific examples, the molecular weights of the proteins in distinguishable bands differ by at least 5 to 30 kDa, for example 10–20 kDa, such as 12 kDa, as shown in FIG. 9. Although the at least eight bands are shown to be distinguishable, the molecular weights of some proteins in the mixture may not be sufficiently different to be resolved separately, and will appear to be overlapping on gel 12. The bands may not be discrete separate bands, as shown in FIG. 2, although for purposes of clarity they are shown as distinct in the drawing. The present invention allows even overlapping proteins to be readily separately identified, as subsequently explained.

As shown in FIG. 3, gradient pattern 26 can be transferred in a conventional fashion to a transfer member 28 electrophoretically, so that the two-dimensional field of separation is maintained with respect to the direction of separation 25. The gradient pattern 26 on transfer member 28 may then be simultaneously exposed to multiple different sets of specific binding agents to identify particular proteins within the mixture, as described below.

The concept of detecting different sets of proteins in each field of exposure is illustrated in FIGS. 4A and 4B. FIG. 4A shows an applicator plate 50, which can be placed onto a transfer member 28. Applicator plate 50 contains a set of four side-by-side elongated slots 64a, 64b, 64c, 64d, each slot having a width W1, and each slot being separated by a width W2. The length of gel chamber 22 in which the protein mixture is placed prior to electrophoresis is at least at great as the total widths of the four slots (4W1) plus the distances between the four slots (3W2). The length of each slot is also of a sufficient length that the slots substantially coincide with a distance the gradient pattern 62 extends in direction of separation 63, such that the slots will apply the antibodies within a two dimensional field of separation that circumscribes and coincides with an outline 84 of gradient pattern 62. However in other embodiments the applicators span only a sub-region of the two dimensional field of separation.

FIG. 4B shows a hypothetical example in which four different sets of antibody mixtures are applied to a transfer member 28 having a protein pattern of separation 62 (shown as discrete bands), in which the proteins have been separated in a direction of separation 63. The four different antibody mixtures are applied from four separate slots 64a, 64b, 64c, 64d in the applicator plate 50 (FIG. 4A), by infusing each mixture, for example under pressure or by capillary action, through a corresponding entrance port 65a, 65b, 65c, 65d and exit port 67a, 67b, 67c, 67d. The imprint of the four slots 64a, 64b, 64c, and 64d, are shown by the corresponding outlines 66a, 66b, 66c, and 66d in FIG. 4B, where the different shading of each of the outlines indicates the imprint of the different antibody mixture that was applied to the substrate from each slot.

In this particular example, none of the antibodies in a mixture applied from one slot recognize the same protein as recognized by any of the antibodies in another mixture in a different slot. After allowing the mixtures of antibodies sufficient time to interact with the proteins in transfer member 28, the mixtures are removed from the slots, for example by suction pressure or capillary action, exerted through the exit ports 67a, 67b, 67c, 67d. The proteins are then detected, for example by using ECL. When detecting the proteins, the entire membrane can be placed in the ECL solution and subsequently exposed to film or a phosphoimager screen to visualize the proteins, although the ECL solution could alternatively be infused through the slots of applicator plate 50.

FIG. 5 shows the results of this hypothetical analysis, in which a sample containing a mixture of nine proteins was separated by electrophoresis in a gel, and transferred to transfer member 28, such as a nitrocellulose membrane, and were analyzed as described in association with FIGS. 4A and 4B. Each of the different sets of antibody mixtures 66a, 66b, 66c, and 66d recognized at least two specific proteins in each field of exposure. In the illustrated example, mixture 66a recognized proteins 24b and 24g, mixture 66b recognized proteins 24a and 24d, mixture 66c recognized proteins 24f and $24h_1$, and mixture 66d recognized proteins 24c, 24e and $24h2$. The protein $24h_1$ recognized by mixture 66c, and protein $24h_2$ recognized by mixture 66d, would have overlapped and been indistinguishable if detected in the same lane. Once the proteins have been identified, they can optionally be quantitated by measuring the intensity of the ECL signal each emits and impregnates a material such as a sensitive screen or x-ray film.

Once the protein signals have been identified, the location of the signals within the field of separation (indicated by the dotted line 84 in FIGS. 4B and 5) can be correlated with an expected location of signals from particular proteins. For example, if the detected signal for protein $24h_1$ corresponds to an expected location for Protein X within the field (for example within the imprint 66c), then protein $24h_1$ is identified as Protein X. Similarly, the locations of the other detected signals in FIG. 5 can be correlated with the expected locations of signals from other known proteins within field of separation 84 (for example within a particular field of exposure such as the imprints of particular lanes 66a–66d), and the different proteins identified in this fashion. Using this technique provides a high-throughput technique for simultaneously identifying (for example) 10, 50, 100, 200, 500 or even 1000 or more proteins simultaneously, depending on the number of antibodies used, and/or the number of lanes, such as the lanes 66 corresponding to the different slots 64.

FIGS. 6–8 show a particular example of an apparatus 130 that can be used to allow multiple different sets of specific binding agents to be exposed to multiple transfer members 128a, 128b. The apparatus 130 shown in FIGS. 6–8 is the MINIBLOTTER device of Levin (U.S. Pat. No. 4,834,946), however other devices can be used in the method of the present invention. Referring to, FIGS. 6–8, apparatus 130 includes an applicator plate 132 and a base plate 134, in between which transfer member 128 may be placed. Applicator plate 132 contains two sets 144a and 144b of applicator slots, and each set includes nine side-by-side elongated slots, each slot having a width W1, and each slot being separated by a width W2. The length of gel chamber 22 (FIG. 1) in which the protein mixture is placed prior to electrophoresis is at least at great as the total widths of the nine slots (9W1) plus the distances between the nine slots (8W2). The length of each slot in each set of slots 144a, 144b is also of a sufficient length that the slots of each series substantially coincide with a distance the gradient pattern 26 (FIGS. 2 and 3) extends in direction of separation 25, such that the slots will apply the antibodies within a two dimensional field that circumscribes and coincides with an outline of gradient pattern 26. For the example shown in FIGS. 6–8, two different transfer members can be simultaneously analyzed by placing a first transfer member 128a under set 144a of the slots (FIG. 8), and a second transfer member 128b under set 144b, and introducing identical sets of antibody mixtures into each of the corresponding slots of series 144a and 144b. Although this particular example shows application of identical sets of antibody mixtures to different transfer members, different sets of antibody mixtures can be used in each set 144a, 144b, and transfer members from electrophoresis gels of the same protein mixture may also be used.

Plates 132, 134 are held together by manually rotatable set screws 136 having a knurled head and an externally threaded shank. FIG. 7 illustrates several screw-receiving holes 138 around the edges of applicator plate 132 through which the screws extend. Screw holes 138 align with the internally threaded holes 140 in base plate 134. To simultaneously expose two different transfer members 128a, 128b (FIG. 8) to multiple different sets of specific binding agents, a cushion sheet 142a, 142b is placed on top of base plate 134 below each set 144a, 144b of the slots to provide a more effective seal. The transfer member 28a, 28b is layered on top of the cushion sheets 142a, 142b, such that the set of applicator slots 144a, 144b on applicator plate 132 extend in direction of separation 25 for each transfer member 128a, 128b. Applicator plate 132 is secured to base plate 134 by tightening screws 136 to compress the plates together, as shown in FIG. 8. This compression closes any gaps between the sets 144a, 144b of the slots, effectively sealing separate applicator slots from one another.

Different sets of specific binding agents (such as liquid mixtures of different antibodies) are introduced through each individual applicator slot, so that each slot applies a unique set of antibodies to the pattern of separation. The liquid mixtures may be introduced into, through and out of each of the individual slots through entrance and exit ports 147, 148. There is a separate entrance and exit port for each slot of the set 144, 145, such that a preselected antibody mixture can be infused under pressure through each slot, to expose a transfer member to the antibody mixture along a lane that corresponds to the area (field of exposure) circumscribed by each slot. Since a different antibody mixture is infused through each of the slots of the set, and the slots are sealed from one another by the pressure of the plates 132, 134 and cushion sheets 142a, 142b, different sets of proteins are detected (if present) in each field of exposure. If protein bands overlap in the direction of separation, they can be distinguished from one another because they are identified in different lanes. In this example, the positions of proteins detected in each lane can be predetermined, and the location of a detected protein correlated with a known location for that lane to identify the protein.

More details about particular aspects of this invention are given in the following examples.

EXAMPLE 1

Simultaneous Detection of Multiple Proteins

This example describes an experiment in which 175 different proteins were identified and quantitated simultaneously. Although this experiment used monoclonal antibodies which recognize signal transduction proteins, other types of antibodies, such as polyclonal antibodies, or other agents that recognize specific proteins, or other types of proteins, can also be used.

Preparation of Lysates from Tissue Culture Cells

Cells were grown to confluency in tissue culture dishes or flasks. After removing the media and rinsing the cells with PBS (20 mls/15 cm plate or flask), approximately 2–3 mls of boiling lysis buffer (10 mM Tris, pH 7.4, 1.0 mM sodium ortho-vanadate, 1.0% SDS) was added. The solution was swirled in the plate to ensure rapid denaturation of cellular proteins. The resulting cell lysate was placed into a 50 ml conical polypropylene tube and microwaved briefly (5–10 seconds). The lysate was subsequently sonicated for 10–30 seconds to shear the DNA present in the cell lysate sample. Alternatively, the lysate can be passed repeatedly through a 26-gauge needle or it can be homogenized with a polytron for about 15–30 seconds. From the resulting sample, a small aliquot (for example 100 $\mu$l) was diluted to 1.0 ml to reduce the SDS concentration to 0.1%, and the total protein content measured using the BCA reagent from Pierce (Rockford, IL). The remainder of the sample was stored at −80° C. for future use.

Preparation of Lysates from Tissues

Recently obtained tissues, or frozen tissues can be prepared as follows. Tissues (0.2 g) were incubated with 3.5 ml of boiling lysis buffer (see above) and homogenized using a polytron at full speed for 15–20 seconds. An equal volume of 2×electrophoresis sample buffer (125 mM Tris pH 6.8, 4% SDS, 10% glycerol, 0.006% bromophenol blue, 2% β-mercaptoethanol) was added and the sample mixed well. Samples can be stored at −80° C. for future use.

Using these methods to prepare lystaes allows fair representation of cellular proteins regardless of the tissue of origin. For example, proteins in the blood can be over-represented, resulting in a false protein content.

Sample Analysis

Jurkat cells (A.T.C.C. #TIB152, Manassas, Va.) were grown to confluence and subsequently treated with or without 100 ng/ml of phorbol 12-myristate 13 acetate (PMA) (Sigma catalog number P8139, St. Louis, Mo.) for 12 hours. Cellular lysates were generated as described above.

Individual samples (0.25 mg protein) were run as a single large lane extending substantially across the width of a 16×16 cm 7.5%–13% gradient SDS-polyacrylimide gel (as in FIG. 1). After electrophoresing the sample to separate the proteins by molecular weight and transferring them electrophoretically to a PVDF membrane, the membrane was placed in a MINIBLOTTER 25 device (see U.S. Pat. No. 4,834,946, incorporated by reference) having 25 side-by-side separate slots that did not communicate with one another, and the applicator and base plates were tightened against the membrane as described in association with FIG. 8 above. A different antibody-containing mixture was infused into each of the different channels of the applicator plate, without permitting cross-contamination between the channels. In this specific example, the sets of different specific binding agents each contained 3–8 different monoclonal antibodies (with the majority including seven different antibodies), each at their optimal concentration. Each set of different antibodies was generated based on the different sizes of the proteins detected by the antibodies, such that the proteins in each field of exposure (lane) would be readily identified by their respective sizes. In one of the channels, a standard set of antibodies is used for every gel to provide molecular weight markers. In this particular example, the standard set of antibodies was run in lane 25 of FIGS. 9A and 9B.

The antibody-containing solution was incubated in the channels for 60 minutes at 25° C. The antibody-containing solutions were removed from the channels, and the channels subsequently washed with buffer (10 mM Tris pH 7.5, 100 mM NaCl, 0.1% Tween-20) to remove unbound antibodies. The membrane was subsequently incubated, after removing the plates, with the secondary antibody anti-mouse IgG-HRP (horseradish peroxidase) for 60 minutes at 25° C. then washed with buffer (100 mM NaCl, 0.1% Tween-20, 5 % non-fat milk) to remove any unbound secondary antibodies. To visualize the proteins, the membrane was incubated with the reagents for enhanced chemiluminescence (Amersham Pharmacia Biotech, or similar reagents from Pierce and other vendors), and the membrane was subsequently exposed to a phosphorimager screen. Alternatively, the membrane can be exposed to film. The resulting signal (either on the screen or on the film) was then captured as a digital image in a digital computer.

The control database contains images of signals that correspond to each of the proteins identified by the antibodies from each applicator slot, at a specified location within the field of protein separation. By comparing the locations of the control image for each lane to the image of the corresponding lane from the experimental gel, every protein in each of the twenty-five channels recognized by the antibodies present in the sets of different specific binding agents was identified. Once the protein is identified, the amount of it present in the transfer member at that location can also be quantitated, using software, for example BioRad Molecular Analyst v.2.1 or Silk Scientific UN-Scan-IT v.3, that correlates brightness of an image with a quantity of a particular protein identified in the field of separation. In this example, using the Silk Scientific software, all of the proteins bands shown in FIGS. 9A and 9B were quantitiated. An example showing how the quantiation was performed for lane 19 from FIGS. 9A and 9B, is shown in FIGS. 10A and 10B (details provided below).

Hence this technique can not only identify a large number of proteins simultaneously, but it can also determine relative quantities of the protein in the original mixture.

As shown in FIGS. 9A and 9B, which are a digital images of actual transfer members that were exposed to the twenty-five different sets of mixtures of antibodies, hundreds of proteins can be visualized simultaneously. Each "lane" (which represents the field of exposure for one set of different specific binding agents that is applied from a single slot in the applicator plate) is compared to the known locations of the proteins the antibodies in that slot recognize.

For example, as shown in FIG. 10A, lane 19 marked (*) in FIGS. 9A (+PMA) and 9B (−PMA) is compared to a control image. The control image contains the predicted location of the proteins recognized by the antibodies in the antibody mixture. FIG. 10A shows how the control image is used to identify the proteins in lane 19 of FIGS. 9A and 9B. FIG. 10B shows how the proteins are quantitated relative to one another, by measuring the relative intensity of each of the protein bands for each lane observed in FIG. 10A. Table 1 shows the relative density of each of the proteins in each sample.

TABLE 1

Relative Density of Proteins Shown in Lane 19 of FIG. 9

| Protein | Jurkat − PMA | Jurkat + PMA | % change* |
|---|---|---|---|
| DSIF (160 kDa) | 169,580 | 83,759.9 | −51% |
| rSec8 (110 kDa) | 102,931 | 61,551 | −40% |
| Annexin VI (70 kDa) | 88,198.8 | 78,153 | −11% |
| PDI (55 kDa) | 14,158 | 7,762.02 | −45% |
| HAX (35 kDa) | 78,385 | 51,034.9 | −35% |
| Bad (23 kDa) | 14,805 | 16,218 | +9.5% |

*Percent by which the level of a specific protein decreased (−) or increased (+), as a result of treating Jurkat cells with PMA.

This analysis allows for the comparative analysis of the same protein in different samples. For example, in the presence of PMA, the protein expression pattern changes in Jurkat cells. The levels of DSIF, rSec8, PDI and HAX proteins decrease, while the levels of the Annexin VI and Bad proteins do not appear to be strongly regulated by the presence of PMA. This same analysis was used to identify, analyze and quantitate the proteins shown in the remaining 24 lanes shown in FIGS. 9A and 9B.

Therefore, this immunoassay method allows for differences in expression of several hundred proteins to be simultaneously analyzed. This parallel analysis of hundreds of fully characterized proteins, using the carefully selected sets of different specific binding agents, significantly saves time.

EXAMPLE 2

Research and Diagnostic Methods

Using the methods described above, the presence and concentrations of a large number of proteins can be compared quantitatively between two or more samples. This simultaneous parallel analysis of proteins can link changes in gene expression (for example during tumor progression) with differences in cellular proteins, such as signal transduction proteins. For example, the method can be used to compare the expression level of a large number of proteins in a normal cell, and a tumor cell of the same cell type.

In this method, cell or tissue lysates are generated from the samples of interest. Such lysates can be obtained from a wide variety of samples, including but not limited to, tissue culture cells, such as those that can be obtained from The American Type Culture Collection, A.T.C.C. (Manassis, Va.); physiological samples, such as whole blood, plasma, serum, urine, or cerebrospinal fluid; and pathology specimens such as biopsies and fine needle aspirates. At the same time, a sample of normal tissue is obtained. Alternatively, if normal tissue is not available, a database containing images of normal tissues (i.e. non-tumor liver, kidney, skin, etc.) which were exposed to each of the antibody mixtures, is used as a comparison. The level of expression observed in the sample from a patient (i.e. liver tumor biopsy) is compared to the expression levels observed for the same proteins in the normal tissue database (i.e. a normal liver sample), to determine if a disease state exists.

The normal and tumor lysates are electrophoresed separately on different gels (although simultaneous for example side-by-side analysis on one gel is possible if more than one receptacle 22 is placed in the gel. Using the method described in Example 1, the proteins are resolved and probed with different sets of specific binding agents. The binding agents recognize proteins, and the expression levels of multiple proteins of interest are compared between the normal and tumor sample. This approach is a cost and time efficient technique for determining differential expression of proteins in normal and neoplastic cells. Moreover, a comparison of protein expression can be made in cells as they progress from normal cells, to cells demonstrating preneoplastic atypia, to carcinoma in situ, and to invasive or metastatic lesions.

Comparisons of relative protein expression at each stage of neoplastic development can provide important clues about biochemical mechanisms of neoplastic transformation. Once these patterns of protein expression are determined, these patterns can be used to diagnose or evaluate tumors, for example by assessing the biochemical profile of the tumor, to assign it to a particular stage of malignant progression. Such information can be used for prognostic purposes, or to select appropriate therapies for a subject from whom the tumor (or other biological material) was obtained.

Examples of other uses of this method include comparing expression of multiple proteins during normal development, and comparing expression of multiple proteins in cells of different lineages (for example stem cells versus adult differentiated cells; fetal versus adult cells; and apoptotic versus proliferating cells).

EXAMPLE 3

Different Sets of Specific Binding Agents

This example describes sets of different specific binding agents that can be used in the present invention. Other sets of different specific binding agents can be generated, using the same principles that were used to generate these sets. The proteins identified by each set are different enough in their molecular weight to be electrophoretically distinguishable from one another. In this example, the specific binding agents are monoclonal antibodies which recognize signal transduction proteins. However, other antibodies, such as polyclonal antibodies, which recognize other proteins (either natural or synthetic), can also be used. In addition, any ligand agent that specifically binds to a protein on a solid surface can be used.

To simply the approach, all available mouse monoclonal antibodies were divided according to the cell lysate which generated an optimal signal for that antibody. For example, all of the antibodies that were previously found to recognize their target protein in the human epitheloid cell line HeLa, were grouped. From this information, antibody mixtures were constructed so that each target protein migrated at least 5–20 kDa, for example 10–20 kDa apart in an acrylamide gel. As shown in FIG. 11A, these antibody mixtures were then applied to a western blot generated from a HeLa cell lysate (see Example 1), both individually and as a complete mixture. Similar antibody mixtures were generated using those that produced a large signal in Jurkat cells, as shown in FIG. 11B. Using this method, dozens of antibody mixtures were generated.

Thus, as is evident from the examples given above, different antibodies with unique specificities can be mixed together to from an antibody mixture which contains, for example, two different antibodies to a maximum number limited only by the gel resolution. Mixing the antibodies does not affect their specificity as shown in FIG. 11. The antibody mixtures generally contain between two and ten different antibodies, and their targets differ by at least 20 kDa in their apparent molecular weight (kDa) (see FIG. 11A, PKAc vs. hILP) or targets that differ by at least 5–10 kDa (see FIG. 11B, Rab 8 vs. Rack-1). Thus, the number of antibodies in a given mixture can be chosen by an "ideal" difference in the molecular weight of their markers. In a gradient gel that separates proteins having molecular weights in the range of 10–250 kDa, for example, 12 different antibodies would be used in a single mixture when a 20 kDa difference in molecular weights is selected. However, since some proteins have multiple isoforms (doublets or triplets) and due to the intrinsic differences in expression (some abundant proteins generate wide bands on the gel) and proteolytic products of different sizes, the number of antibodies, for example, can be limited to about 10 different in a given mixture. The process of generating mixtures is long and tedious, it requires testing individual antibodies and mixtures in different lysates until all signals generated can be positively identified.

TABLE 2

A Few Examples of Mixtures of Specific Binding Agents

| | Molecular Weight (kDa) | Protein Recognized | Antibody Dilution |
|---|---|---|---|
| Set 1 | 150 | Integrin a5 | 1:2500 |
| | 110 | LRP | 1:250 |
| | 90 | Hsp90 | 1:1000 |
| | 74 | PKC iota | 1:200 |
| | 51 | PKA RII alpha | 1:100 |
| | 40/25 | CRK | 1:2500 |
| Set 2 | 250 | RPTP β | 1:250 |
| | 200 | L1 | 1:2000 |
| | 110 | LAMP-1 | 1:100 |
| | 80 | BMX | 1:1000 |
| | 68 | PTP1C | 1:500 |
| | 48 | RBBP | 1:1000 |
| | 36 | apoE | 1:1000 |
| | 21 | Rho | 1:250 |
| Set 3 | 240 | Fibronetin | 1:2000 |
| | 180 | EGF-r cl. 13 | 1:5000 |
| | 117 | Rabaptin 5 | 1:50 |
| | 62 | STI-1 | 1:250 |
| | 46 | MEK2 | 1:3000 |
| | 25 | Ran | 1:5000 |
| | 19 | p19 Skp | 1:5000 |

TABLE 2-continued

A Few Examples of Mixtures of Specific Binding Agents

| | Molecular Weight (kDa) | Protein Recognized | Antibody Dilution |
|---|---|---|---|
| Set 4 | 300 | IP3-r | 1:1000 |
| | 149 | AKAP149 | 1:500 |
| | 92 | β-catenin | 1:1000 |
| | 60–80 | CLA-1 | 1:1000 |
| | 46 | FTPase β | 1:250 |
| | 36 | REF-1 | 1:250 |
| | 27 | p27 Kip1 | 1:1000 |
| Set 5 | 465 | DNA-PKcs | 1:250 |
| | 220 | ZO-1 | 1:100 |
| | 105 | KRIP-1 | 1:1000 |
| | 69 | ERp72 | 1:250 |
| | 48 | ICH-1L | 1:250 |
| | 31 | Syntaxin 6 | 1:1000 |
| | 22 | Alg-2 | 1:1000 |

In view of the many possible embodiments to which the principles of the invention may be applied, it should be recognized that the illustrated embodiments are only particular examples of the invention and should not be taken as a limitation on the scope of the invention. For example, instead of applying the slots simultaneously to the transfer member, the slots could be applied sequentially. Infusion of antibody mixtures from a supply source into the slots through ports can also be replaced with other infusion methods, and reference positions of bands within the field of separation can be replaced by detection of reference positions within a field of exposure. Hence, the scope of the invention is defined by the following claims. We therefore claim as our invention all that comes within the scope and spirit of these claims.

We claim:

1. A method for identifying different proteins in a protein mixture sample, comprising:
    (a) introducing said protein mixture into an elongated sample chamber in an electrophoresis gel;
    (b) performing one-dimensional electrophoresis to separate the proteins by molecular weight in a direction of separation that extends transverse to the sample chamber to obtain a molecular weight gradient pattern consisting of a plurality of bands transverse to the direction of separation;
    (c) exposing said pattern obtained in step (b) to a plurality of adjacent, specific binding agent applicators that extend in the direction of separation; and
    (c) applying through each applicators different sets of specific binding agents, wherein each set recognizes proteins of sufficiently different molecular weights to distinguish different proteins from one another along the direction of separation.

2. The method of claim 1, wherein the applicators comprise at least three elongated applicators, each of which applies at least 2 different specific binding agents.

3. The method of claim 2, wherein the applicators apply a total of at least 10 different specific binding agents.

4. The method of claim 3, wherein the applicators apply a total of at least 50 different specific binding agents simultaneously.

5. The method of claim 2, wherein a ratio of different specific binding agents applied to a number of applicators is at least 1 different specific binding agent to each applicator.

6. The method of claim 5, wherein the ratio of different specific binding agents applied to the number of applicators is at least 3 different specific binding agents to each applicator.

7. The method of claim 2, wherein the applicators comprise at least ten applicators.

8. The method of claim 1, wherein the applicators comprise at least three elongated applicators, each of which applies at least 6 different specific binding agents.

9. The method of claim 1, wherein the applicators extend substantially parallel to one another.

10. The method of claim 1, wherein the applicators comprise slots in au applicator plate.

11. The method of claim 10, wherein the applicators further comprise elongated channels that communicate with the slots through which the specific binding agents are applied.

12. The method of claim 1, wherein the specific binding agents are antibodies.

13. The method of claim 12, wherein the antibodies are monoclonal antibodies.

14. The method of claim 1, wherein the protein sample mixture comprises a cell lysate.

15. The method of claim 1, wherein the specific binding agents recognize signal transduction proteins.

16. The method of claim 1, further comprising after exposing the pattern to the specific binding agents, detecting a location of binding of specific binding agents and correlating each location with a particular specific binding agent that identifies a protein of interest.

17. The method of claim 16, further comprising after detecting the protein of interest, quantitating the protein of interest.

18. The method of claim 1, wherein the pattern is transferred from the gel to a transfer member, and the different sets of specific binding agents are applied to the transfer member.

19. The method of claim 1, wherein the different proteins are separated by molecular weight and are of sufficiently different molecular weights to distinguish the different proteins from one another.

20. A method for simultaneously identifying different proteins in a protein mixture, comprising:
    introducing the protein mixture into an elongated sample chamber in an electrophoresis gel;
    performing one-dimensional electrophoresis on the protein mixture to separate the proteins in the mixture in a direction of separation that extends transverse to the sample chamber into a molecular weight gradient pattern consisting of a plurality of bands transverse to the direction of separation;
    exposing the pattern simultaneously to a plurality of adjacent, elongated antibody applicator channels having slots that extend in the direction of separation;
    applying through each slot a different sets of specific binding agents, wherein the specific binding agents within each set recognize proteins of distinguishable molecular weights, and different proteins that have similar molecular weights are detected by specific binding agents applied through different slots; and
    detecting one or more locations of binding of the specific binding agents along each channel, and correlating each location with a particular specific binding agent that identifies a protein of interest.

21. The method of claim 20, wherein the specific binding agents comprise antibodies.

22. The method of claim 20, wherein at least three different specific binding agents are applied through each slot, and a total of at least 50 different specific binding agents are applied through all the slots.

23. The method of claim 20, wherein correlating each location comprises comparing a detected location with a database of potential locations for each applicator, wherein each potential location is associated with a protein of interest.

24. A method of simultaneously identifying different proteins in a cell lysate sample, comprising:
    introducing the cell lysate sample into an elongated sample chamber in an electrophoresis gel;
    performing one-dimensional electrophoresis on the sample to separate the proteins in the cell lysate in a direction of separation that extends transverse to the sample chamber into a molecular weight gradient pattern consisting of a plurality of bans transverse to the direction of separation;
    transferring the pattern to a transfer member;
    exposing the pattern on the transfer member simultaneously to a plurality of adjacent, elongated antibody applicator channels having slots that extend in the direction of separation;
    applying through each of the plurality of applicators a liquid containing a set of specific binding agents, wherein liquids applied through different applicators contains different sets of specific binding agents, wherein the specific binding agents within each set recognize proteins of distinguishable molecular weights, and wherein the specific binding agents in different sets are substantially different to recognize a variety of different proteins of interest; and
    detecting one or more locations of binding of the specific binding agents, and correlating each location with a particular specific binding agent that identifies a protein of interest, by comparing a detected location of binding with an expected location of binding for each applicator, wherein there are at least fifty different specific binding agents applied by the applicators.

25. A method for simultaneously analyzing a plurality of different proteins in a sample, comprising:
    introducing the sample into al elongated sample chamber in an electrophoresis gel;
    subjecting the sample to one-dimensional electrophoresis, thereby separating the plurality of different proteins by molecular weight in a direction of separation that extends transverse to the sample chamber to obtain a molecular weight rent pattern consisting of a plurality of bands transverse to the direction of separation;
    transferring and immobilizing the plurality of different proteins to a transfer member;
    placing the transfer member between an upper and a lower plate of a device containing several discrete slots in one of the plates wherein the slots are oriented to extend in the direction of seperation;
    applying through said slots different antibody-containing mixtures, each mixture containing a different set of antibodies;
    exposing each antibody-containing mixture to the surface of the transfer member for a sufficient period of time for an antibody to bind to a protein of interest if the protein is present in the transfer member;
    detecting antibodies within the antibody-containing mixtures bound to proteins of interest in the transfer member; and
    correlating the detected antibodies with expected locations of binding of proteins of interest.

26. The method of claim 25 wherein the transfer member is a protein transfer membrane.

27. The method of claim 25 wherein the sample is a cell lysate.

28. The method of claim 25 wherein at least two different sets of antibodies recognize proteins that would not be distinguishable in the field of separation if the two different sets of antibodies were applied through a single slot.

29. The method of claim 25 wherein each antibody-containing mixture contains at least two different antibodies.

30. The method of claim 25 wherein each antibody-containing mixture contains at least ten different antibodies.

31. The method of claim 25 wherein the total number of different antibodies applied per transfer member is 50–250.

32. The method of claim 25 wherein the ratio of different sets of antibody-containing mixtures to the number of slots through which the antibody-containing mixture is applied is 1:1.

33. The method of claim 25 where the number of different antibodies applied through each of the slots ranges from 2 to 10.

34. The method of claim 25 wherein the number of different antibodies applied through each of the slots ranges from 1–20.

35. The method of claim 25 wherein the plate that contains the slots contains at least twenty different slots.

36. The method of claim 35 wherein the plate that contains the slots contains at least 50 channels.

37. The method of claim 25 wherein the proteins of interest range in molecular weight from 10 kDa–300 kDa.

* * * * *